US008487047B2

(12) United States Patent

(10) Patent No.: US 8,487,047 B2

Zhernosekov et al.

(45) Date of Patent: Jul. 16, 2013

(54) $^{68}$GA GENERATOR

(75) Inventors: Konstantin Zhernosekov, Munich (DE); Tuomo Nikula, Ottobrunn (DE)

(73) Assignee: ITM Isotopen Technologien Munchen AG, Garching (DE)

( * ) Notice: Subject to any disclaimer, the term of this patent is extended or adjusted under 35 U.S.C. 154(b) by 58 days.

(21) Appl. No.: 13/247,381

(22) Filed: Sep. 28, 2011

(65) Prior Publication Data

US 2012/0252981 A1 Oct. 4, 2012

(51) Int. Cl.

*C08F 20/44* (2006.01)

*C07K 7/00* (2006.01)

(52) U.S. Cl.

USPC .................. 525/329.2; 525/330.3; 525/333.3; 530/328

(58) Field of Classification Search

USPC .......... 525/329.2, 330.3, 333.3; 530/327–330

See application file for complete search history.

(56) References Cited

U.S. PATENT DOCUMENTS

| | | | |
|---|---|---|---|
| 4,264,468 A | 4/1981 | Neirinckx et al. | |
| 4,333,911 A | 6/1982 | Comar et al. | |
| 7,011,816 B2 | 3/2006 | Griffiths et al. | |
| 7,023,000 B2 | 4/2006 | Zyuzin | |
| 2007/0009409 A1 | 1/2007 | Gali et al. | |
| 2010/0202915 A1 * | 8/2010 | Zhernosekov et al. | 420/1 |

FOREIGN PATENT DOCUMENTS

| | | |
|---|---|---|
| AT | 334084 | 12/1976 |
| GB | 2056471 | 3/1981 |
| JP | 2008108311 | 2/2008 |

* cited by examiner

*Primary Examiner* — Michael G Hartley

*Assistant Examiner* — Jagadishwar Samala

(74) *Attorney, Agent, or Firm* — Lewis Kohn & Fitzwilliam LLP; David M. Kohn; Kari Moyer-Henry

(57) ABSTRACT

The present invention relates to a $^{68}$Ga generator, wherein the $^{68}$Ge parent nuclide thereof is attached specifically to a support through a triethoxyphenyl group and continuously disintegrates to $^{68}$Ga, the triethoxyphenyl group being covalently bound to a support material through a linker.

9 Claims, No Drawings

$^{68}$GA GENERATOR

PRIORITY INFORMATION

This application is a United States Non-provisional Application claiming priority under 35 U.S.C. §119 from German Patent Application No. DE 102010037964.6, filed Oct. 5, 2010, the entire contents of which are herein incorporated by reference.

FIELD OF THE INVENTION

The present invention relates to a generator for a $^{68}$ Gallium ($^{68}$Ga) daughter nuclide wherein the $^{68}$Germanium ($^{68}$Ge) parent nuclide thereof is attached specifically to a support through a trihydroxyphenyl group or a dihydroxyphenyl group and continuously disintegrates to $^{68}$Ga by electron capture at a half-life of 270.82 days.

DETAILED DESCRIPTION OF THE INVENTION

Radionuclides of the positron emitter type are employed in the so-called positron emission tomography. Positron emission tomography (PET), being a variant of emission computer tomography, is an imaging method of nuclear medicine which produces sectional images of living organisms by visualizing the distribution of a weakly radiolabelled substance (radiopharmaceutical) in the organism to thereby image biochemical and physiological functions, and thus pertains to the diagnostic division of so-called functional imaging. In the framework of such a PET examination on a patient, the distribution of a weakly radioactive positron emitter-labeled substance within an organism is visualized by means of the radioactive decay of the positron emitter, as a general rule with the aid of several detectors.

In particular, based on the principle of scintigraphy, a radiopharmaceutical is administered intravenously to the patient at the beginning of a PET examination. PET uses radionuclides that emit positrons ($\beta^+$ radiation). Upon interaction of a positron with an electron in the patient's body, two highly energetic photons are emitted in precisely opposite directions, i.e., at a relative angle of 180 degrees. In terms of nuclear physics, this is the so-called annihilation radiation. The PET apparatus typically includes a multiplicity of detectors for detecting the photons that are annularly disposed around the patient. The principle of the PET examination consists in recording coincidences between two respective opposed detectors. The temporal and spatial distribution of these recorded decay events allows one to infer the spatial distribution of the radiopharmaceutical inside the body and in particular inside the organs that are of interest for the respective examinations, and/or pathological changes such as space-occupying processes. From the obtained data a series of sectional images is calculated, as is usual in computer tomography. PET is frequently employed in metabolism-related investigations in oncology, neurology, as well as cardiology, however an increasing number of additional fields of application has been surfacing in recent times.

The nuclide hitherto finding the widest application in PET is the radioactive isotope $^{18}$Flourine ($^{18}$F). It is produced with the aid of a cyclotron and may be transported—owing to its relatively long half-life of about 110 minutes—over somewhat greater distances from the cyclotron to a nuclear-medical unit of a hospital. For this reason it is presently still the nuclide that is used most frequently in PET examinations.

Apart from $^{18}$F, $^{11}$Carbon ($^{11}$C), $^{13}$Nitrogen ($^{13}$N), $^{15}$Oxygen (150), $^{86}$Ga, $^{64}$Copper ($^{64}$Cu) or $^{82}$Rubidium ($^{82}$Rb) are mainly used.

The half-life values of these isotopes are shown in Table 1.

TABLE 1

| Nuclide | Half-life |
|---|---|
| $^{11}$C | 20.3 minutes |
| $^{13}$N | 10.1 minutes |
| $^{15}$O | 2.03 minutes |
| $^{18}$F | 110 minutes |
| $^{68}$Ga | 67.63 minutes |
| $^{64}$Cu | 12.7 hours |
| $^{82}$Rb | 1.27 minutes |

$^{68}$Ga and $^{82}$Rb are generator radioisotopes. The radioisotope here comes into existence through decay of an unstable parent isotope inside a nuclide generator wherein it accumulates. All of the other named PET nuclides are produced with the aid of a cyclotron.

Based on the half-life values specified in Table 1 and the production methods for the radionuclides, the following consequences result for PET examinations: The use of $^{11}$C necessitates the presence of a cyclotron in relative vicinity of the PET system. If the comparatively short-lived $^{13}$N or $^{15}$O nuclides are employed, the cyclotron must be located in immediate vicinity of the PET scanner. A radiopharmaceutical production facility equipped with a cyclotron does, however, require an investment in the range of tens of millions, which represents a massive economic limitation of the utilization of the nuclides produced in the cyclotron for PET.

This is one reason among others why generator radioisotopes and in particular $^{68}$Ga are of particular interest for nuclear medicine and especially for the PET process.

In order to be able to perform a PET, a radionuclide is coupled to a molecule (covalently bonded or also in the form of a coordinative bond) that is a metabolic participant or otherwise presents a biological and/or pharmacological effect, such as bonding to a specific receptor.

A typical molecule used in prior-art PET examinations is $^{18}$F-fluorodesoxyglucose (FDG). As FDG-6-phosphate is not metabolized further following in-vivo phosphorylation, an accumulation ("metabolic trapping") takes place. This is of particular advantage for the early diagnosis of cancerous diseases. In addition to the localization of tumors and metastases, however, the distribution of FDG in the body generally permits conclusions as to the glucose metabolism of tissues.

For PET with $^{68}$Ga, for instance, a $^{68}$Ga-DOTATOC chelate having the following structure is used:

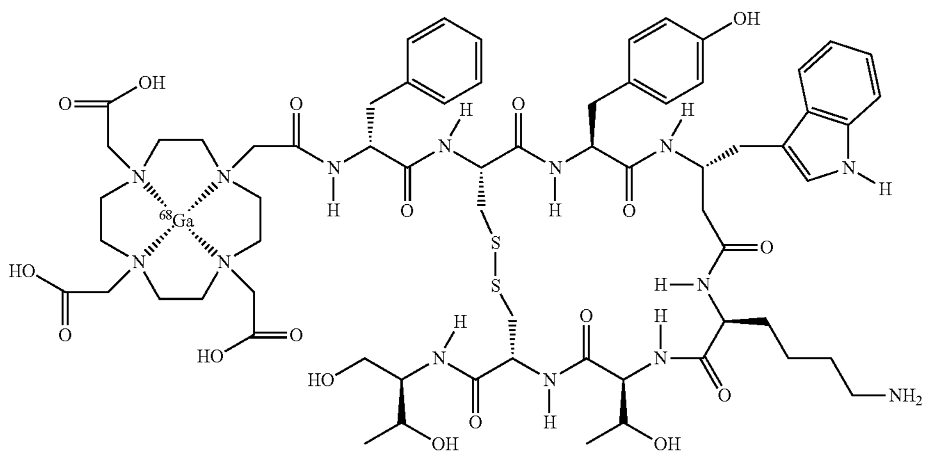

By means of a like $^{68}$Ga-DOTA-d-Phe(1)-Tyr(3)-octreotid ($^{68}$Ga-DOTATOC) it is possible, for example, to detect and localize neuroendocrine tumors as well as their metastases with the aid of imaging methods such as PET. In particular it is possible to detect somatostatin-expressing tumors and their metastases with the aid of positron emission tomography. The $^{68}$Ga-DOTATOC accumulates at the correspondingly degenerated cells. These areas emit distinctly higher radiation in comparison with the normal tissue. The radiation is localized by means of detectors and processed into a three-dimensional representation by image processing.

In view of the above, gallium-68 is a radionuclide that is highly interesting for PET, with new sources of access being of great importance for clinical diagnostics and research.

$^{68}$Ga may be obtained by means of a germanium-68/gallium-68 radionuclide generator system such as is known, e.g., from European patent application EP 2216789 A1.

The $^{68}$Ga disintegrates at a half-life of 67.63 minutes while emitting a positron. As was mentioned in the foregoing, the physical-chemical properties of gallium-68 make it very well suited for nuclear-medical examinations.

It is known from nuclear-physical examinations that $^{68}$Ga may be generated by electron capture from the parent nuclide $^{68}$Ge which disintegrates at a half-life of 270.82 days.

In a $^{68}$Ga generator, the $^{68}$Ge is typically bound to an insoluble matrix of an inert support, and due to the continuous decay of the germanium, $^{68}$Ga keeps being formed continuously and may be extracted from the generator by elution with a solvent.

In order to prepare radiopharmaceuticals it is necessary to put high quality demands to the radionuclides used. In particular, the radionuclides produced have to have a high degree of purity and must be substantially free of metallic impurities, for owing to competing reactions these may have an adverse effect on the labeling of the radiopharmaceuticals, and may reduce the technically achievable yield. In addition, metallic impurities may interfere with the sensitive biomedical measuring systems.

From US 2007/0009409 A1, for example, radionuclide generators are known wherein the parent nuclide bonds to an oxygen-containing functional group which is appended to an organic linker in turn bound to an inorganically linked network. What is described, e.g., are $^{212}$Bi or $^{213}$Bi generators, wherein the parent nuclide may be $^{224}$Ra, $^{225}$Ra, or $^{225}$Ac. The exchanger material may, e.g., be formed of covalently linked inorganic oxides that are capable of forming oxygen-linked networks. The functional groups may include sulfato groups, in particular —$SO_3H$, —$SO_3Na$, —$SO_3K$, —$SO_3Li$, —$SO_3NH_4$, or may be selected from —$PO(OX)_2$ or —COOX, with X being selected from among H, Na, K, or $NH_4$ or combinations of these.

GB 2 056 471 A further describes an ion exchanger for separating gallium-68 from its parent nuclide germanium-68. The ion exchanger according to GB 2 056471 A consists entirely or substantially of a condensation product obtained from a polyhydroxybenzene having not less than two adjacent hydroxyl groups and formaldehyde in a molar excess of 5 to 15%, or contains such a condensation product incorporated therein, wherein the condensation product has a reversible water content of not less than 40% by weight. In order to elute the formed $^{68}$Ga from the ion exchanger, the ion exchanger material must be treated with bound $^{68}$Ge with 2M to 5M HCl.

The high acid concentration on the one hand, as well as the toxic effects of the formaldehyde used as a co-monomer, make reprocessing of the eluate necessary prior to its use as a radiopharmaceutical.

In addition, the method for synthesizing a di- or trihydroxyphenol formaldehyde resin is technically complex and cost-intense.

In comparison with this prior art, the method of EP 2216789 A1 already constituted a clear progress, for in this application a polyhydroxyphenol was bonded to a hydrophobic group of molecules which was selected from the group comprising: an aromatic or heteroaromatic group; a fatty acid, saturated or unsaturated, having more than three C atoms; a branched or unbranched alkyl chain having more than three C atoms such as, e.g., octyl, decyl, or octadecyl groups; and an organic support or an inorganic support material such as resin and silica gel were coated with this molecule in the absence of a covalent bond. From the column material thus coated, small chromatographic columns were produced which were charged with an aqueous solution of a $^{68}$Ge salt, wherein the $^{68}$Ge was adsorbed quantitatively on the columns.

The column materials were then eluted with 0.05 M HCl, wherein the eluate substantially contained $^{68}$Ga, and the breakthrough of the parent nuclide was in a range from $1.0\times10^{-5}$ to $3\times10^{-3}$%.

Despite the fact that the gallium-68 could be used directly and without further chemical reprocessing for the preparation of injectable gallium-68 radiopharmaceuticals, the hydrophobic compound to which the polyhydroxyphenol was coupled detached in the course of time and resulted in impurities of the desired $^{68}$Ga nuclide, so that prior to the utilization as a radiopharmaceutical after a certain service time of the support materials, a further purification step was nevertheless necessary before the $^{68}$Ga fraction could be employed for preparing a radiopharmaceutical.

Starting out from the prior art of EP 2216789 A1, it is therefore an object of the present invention to provide a stable gallium-68 generator which can be used repeatedly over a prolonged period of time without having to further process the gallium-68 fraction prior to its use for the preparation of a radiopharmaceutical.

This object is achieved through a generator for a $^{68}$Ga daughter wherein the $^{68}$Ge parent nuclide thereof is attached specifically to a support through a trihydroxyphenyl group or a dihydroxyphenyl group and continuously disintegrates to $^{68}$Ga by electron capture at a half-life of 270.82d, characterized in that the trihydroxyphenyl group or dihydroxyphenyl group is covalently bound via a linker to a support material, the linker being selected from the group consisting of: $C_2$ to $C_{20}$ esters; $C_2$ to $C_{20}$ alkyls, phenyl, thiourea, $C_2$-$C_{20}$ amines, maleimide, melamine, trihydroxyphenyl alkoxsilanes, in particular 1,2,3-trihydroxyphenyltriethoxysilane, 1,2,3-trihydroxyphenyldiethoxysilane, 1,2,3-trihydroxyphenylethoxysilane, 1,2,3-trihydroxyphenyltripropoxysilane, 1,2,3-trihydroxyphenylchlorosilane, epichlorohydrin, isothiocyanates, thiols.

A preferred embodiment of the present invention is a $^{68}$Ga generator wherein the support material is selected from the group consisting of: inorganic inert oxide materials, in particular silica gel, $SiO_2$, $TiO_2$, $SnO_2$, $Al_2O_3$, ZnO, $ZrO_2$, $HfO_2$ or organic inert polymers and copolymers, in particular styrene-divinylbenzene, polystyrene, styrene-acrylonitrile, styrene-acrylonitrile-methylmethacrylate, acrylonitrile-methylmethacrylate, polyacrylonitrile, polyacrylates, acrylic or methacrylic esters, acrylonitrile-unsaturated dicarboxylic acid-styrene, vinylidene chloride-acrylonitrile.

If is preferred if the trihydroxyphenyl group is 1,2,3-trihydroxybenzene (pyrogallol), wherein it is preferredly possible to employ silica gel as a support material and 1,2,3-trihydroxyphenyltriethoxysilane as a linker.

The silica gel typically has an average particle size of 10-150 μm and an average pore size of 6-50 nm.

A treatment of the $^{68}$Ge-charged trihydroxyphenyl group of the support material for obtaining the $^{68}$Ga ions formed by radioactive decay of the parent nuclide with 0.05 to 0.5 M HCl was found to be a preferred, highly specific elution method.

For the $^{68}$Ga generator of the present invention, $^{68}$Ge salts in the form of a compound having the oxidation value IV are preferredly employed for charging the support material.

In particular, an aqueous solution of a $^{68}$Ge(IV) salt is employed for attaching $^{68}$Ge to the trihydroxyphenyl group; with $^{68}$Ge aqua ions being particularly preferred.

With the $^{68}$Ga generator according to the present invention, the produced $^{68}$Ga possesses a purity permitting immediate radiopharmaceutical utilization, with the content of impurities, in particular metallic impurities, being in a range from 10 to 100 ppb (by mass), preferably between 1 and 10 ppb (by mass), and in a particularly preferred manner less than 1 ppb (by mass).

Notwithstanding the fact that covalent couplings such as silane or epichlorohydrin or isothiocyanate couplings of organic molecules or biomolecules to an inert inorganic or organic support have in principle been known for a long time in the state of the art, it is equally known that such couplings are subject to hydrolysis when acids are used as eluting agents. As a result of this acid hydrolysis the support would irreversibly be destroyed upon prolonged use, which in turn would equally lead to contaminations of the $^{68}$Ga fraction.

It was, however, surprisingly found in practical tests involving in particular silane coupling agents, that these are acid-stable over a prolonged time period and result in highly pure $^{68}$Ga fractions if the support materials of the present invention charged with $^{68}$Ge are eluted with 0.05 M to 0.5 M HCl in order to leach the $^{68}$Ga from the support material charged with the parent nuclide.

The generator of the invention for a $^{68}$Ga daughter nuclide which is formed from a $^{68}$Ge parent nuclide thus for the first time provides a $^{68}$Ga generator having long-time stability, wherein the obtained $^{68}$Ga fraction may be used directly as a radiopharmaceutical, for example for PET.

Further advantages and features of the present invention become evident from the description of a practical example.

Example

A germanium-specific resin was prepared by treating an inert silica gel having a particle size of approx. 40 μm and a pore size of approx. 6 nm with 1,2,3-trihydroxyphenyltriethoxysilane. Silanization of the native silica gel resulted in covalently bonded 1,2,3-trihydroxybenzene functional groups on the inert support. Measurements of the weight distribution factors of Ge(IV) on the resin confirmed the high affinity of the material with germanium. The resin was utilized in the form of small chromatographic columns.

Aqueous solutions including HCl or $HNO_3$ or NaCl of the radionuclide $^{68}$Ge and having activities in a range from 100 to 1000 MBq were pumped through the columns. Due to the specific bond of the $^{68}$Ge, the latter was quantitatively adsorbed, or attached, on the column materials.

These $^{68}$Ge-charged columns were used to produce the short-lived daughter nuclide $^{68}$Ga. While $^{68}$Ge is attached on the support, $^{68}$Ga is continuously formed and may be eluted repeatedly. The highly specific elution of $^{68}$Ga may be carried out effectively in weak hydrochloric solutions (0.05 to 0.5 M HCl) having small volumes of up to 2.5 ml. The breakthrough of the parent nuclide $^{68}$Ge was on the order of $<10^{-5}$%.

The $^{68}$Ga thus obtained could be used directly, i.e. without any chemical reprocessing, in order to prepare injectable $^{68}$Ga radiopharmaceuticals.

In addition, the resin of the invention may be used for removing any traces of germanium (both radioactive and stable isotopes) from aqueous solutions for analytical or pharmaceutical applications.

Due to a covalent coupling to the support material, the resin exhibits an increased chemical and radiolytic stability in comparison with the prior art of EP 2 216 789 A1, as well as improved chemical-mechanical properties such as a lower hydrodynamic resistance.

We claim:

1. A generator for a $^{68}$Gallium ($^{68}$Ga) daughter nuclide, wherein the $^{68}$Germanium ($^{68}$Ge) parent nuclide thereof is attached specifically to a support through a trihydroxyphenyl group or a dihydroxyphenyl group and continuously disintegrates to $^{68}$Ga by electron capture at a half-life of 270.82d, wherein the trihydroxyphenyl group or dihydroxyphenyl group is covalently bound via a linker to a support material, the linker being selected from the group consisting of: $C_2$ to $C_{20}$ esters; $C_2$ to $C_{20}$ alkyls, phenyl, thiourea, $C_2$-$C_{20}$ amines, maleimide, melamine, trihydroxyphenyl alkoxsilanes, in particular 1,2,3-trihydroxyphenyltriethoxysilane, trihydroxyphenyldiethoxysilane, 1,2,3-trihydroxyphenylethoxysilane, 1,2,3-trihydroxyphenyltripropoxysilane, 1,2,3-trihydroxyphenylchlorosilane, epichlorohydrin, isothiocyanates, thiols.

2. The $^{68}Ga$ generator of claim 1, wherein the support material is selected from the group consisting of: inorganic inert oxide materials, in particular silica gel, $SiO_2$, $TiO_2$, $SnO_2$, $Al_2O_3$, ZnO, $ZrO_2$, $HfO_2$, organic inert polymers and copolymers, in particular styrene-divinylbenzene, polystyrene, styrene-acrylonitrile, styrene-acrylonitrile-methylmethacrylate, acrylonitrile-methylmethacrylate, polyacrylonitrile, polyacrylates, acrylic or methacrylic esters, acrylonitrile-unsaturated dicarboxylic acid-styrene, vinylidene chloride-acrylonitrile.

3. The $^{68}Ga$ generator of claim 1, wherein the trihydroxyphenyl group is 1,2,3-trihydroxybenzene (pyrogallol).

4. The $^{68}Ga$ generator according of claim 1, wherein silica gel is employed as a support material, and 1,2,3-trihydroxyphenyltriethoxysilane is employed as a linker.

5. The $^{68}Ga$ generator of claim 4, wherein the silica gel has an average a particle size of 10-150 μm and an average pore size of 6-50 nm.

6. The $^{68}Ga$ generator of claim 4, wherein the $^{68}Ge$-charged trihydroxyphenol group of the support material is treated with 0.05 to 0.5 M HCl for specifically eluting the $^{68}Ga$ ions formed by radioactive decay of the parent nuclide.

7. The $^{68}Ga$ generator of claim 1, wherein the parent nuclide $^{68}Ge$ is employed in the form of a compound having the oxidation value IV.

8. The $^{68}Ga$ generator of claim 7, wherein an aqueous solution of a $^{68}Ge(IV)$ salt is employed for attaching $^{68}Ge$ to the trihydroxyphenol group, in particular $^{68}Ge$-aqua ions.

9. The $^{68}Ga$ generator of claim 1, wherein the produced $^{68}Ga$ possesses a purity permitting its direct radiopharmaceutical utilization, with the content of impurities, in particular metallic impurities, being in a range from 10 to 100 ppb (by mass), preferably between 1 and 10 ppb (by mass), and in a particularly preferred manner less than 1 ppb (by mass).

* * * * *

UNITED STATES PATENT AND TRADEMARK OFFICE

CERTIFICATE OF CORRECTION

PATENT NO. : 8,487,047 B2
APPLICATION NO. : 13/247381
DATED : July 16, 2013
INVENTOR(S) : Zhernosekov et al.

It is certified that error appears in the above-identified patent and that said Letters Patent is hereby corrected as shown below:

In the Claims:

Col. 5, line 23: the word "alkoxsilanes" should be replaced with "alkoxysilanes";

Col. 5, line 39: the first occurrence of "If" should be replaced with "It";

Col. 5, line 39: the second occurrence of "if" should be deleted;

Col. 6, line 65: the word "alkoxsilanes" should be replaced with "alkoxysilanes"; and Col. 8, line 2: the word "a" between "average" and "particle" should be deleted.

Signed and Sealed this
Third Day of September, 2013

Teresa Stanek Rea
*Acting Director of the United States Patent and Trademark Office*